(12) United States Patent
Nemeh et al.

(10) Patent No.: US 7,494,078 B2
(45) Date of Patent: Feb. 24, 2009

(54) PROCESS AND PRODUCTS OF CHINESE KAOLIN

(75) Inventors: Saad N. Nemeh, Ellicott City, MD (US); Danny Williams, Macon, GA (US); Francis Yin, Shuozhou (CN); Randall P. Brown, Macon, GA (US); Ernie Finch, Macon, GA (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 11/845,614

(22) Filed: Aug. 27, 2007

(65) Prior Publication Data

US 2007/0290085 A1    Dec. 20, 2007

Related U.S. Application Data

(62) Division of application No. 10/777,328, filed on Feb. 12, 2004, now Pat. No. 7,279,037.

(51) Int. Cl.
*B02C 19/00* (2006.01)
*B02C 9/04* (2006.01)

(52) U.S. Cl. .................. 241/36; 241/101.2; 241/101.3

(58) Field of Classification Search ............. 241/33–37, 241/65, 101.2, 101.3
See application file for complete search history.

(56) References Cited

U.S. PATENT DOCUMENTS

| | | | |
|---|---|---|---|
| 3,171,718 A | 3/1965 | Gunn et al. | |
| 3,383,438 A | 5/1968 | Allegrini et al. | |
| 3,586,523 A | 6/1971 | Fanselow et al. | |
| 3,941,872 A | 3/1976 | Puskar | |
| 4,246,039 A | 1/1981 | Mixon, Jr. | |
| 5,011,534 A | 4/1991 | Berube et al. | |
| 5,050,808 A * | 9/1991 | Satake et al. | 241/37 |
| 5,261,965 A | 11/1993 | Dunaway et al. | |
| 5,516,364 A | 5/1996 | Brantley et al. | |
| 5,624,488 A | 4/1997 | Forbus et al. | |
| 5,713,998 A | 2/1998 | Shurling, Jr. et al. | |
| 5,856,397 A | 1/1999 | Pope et al. | |
| 5,997,626 A | 12/1999 | Wu et al. | |
| 6,136,086 A | 10/2000 | Hen et al. | |
| 6,238,473 B1 | 5/2001 | Maxwell et al. | |
| 6,416,732 B1 | 7/2002 | Curran et al. | |

* cited by examiner

*Primary Examiner*—Faye Francis
(74) *Attorney, Agent, or Firm*—Bernard Lau

(57) ABSTRACT

Disclosed are methods of processing Chinese kaolin involving providing Chinese kaolin having a desired powder size, delaminating the Chinese kaolin, pulverizing the delaminated Chinese kaolin at least two times, and heating the at least twice pulverized Chinese kaolin. Also disclosed are systems for automated processing of Chinese kaolin containing a pulverizer for pulverizing Chinese kaolin, a tester for testing and generating data of at least one parameter of the Chinese kaolin or at least one parameter of the pulverizer, a controller, operatively coupled to the pulverizer and the tester, for controlling operation of the pulverizer based on data received from the tester.

20 Claims, 4 Drawing Sheets

PROCESS AND PRODUCTS OF CHINESE KAOLIN

CROSS-REFERENCE TO RELATED APPLICATIONS

This application claims the benefit of and is a Divisional application of co-pending application Ser. No. 10/777,328 filed on Feb. 12, 2004, which is hereby incorporated by reference.

FIELD OF THE INVENTION

The present invention generally relates to processes and products that are made using Chinese kaolin, also known as Shanxi kaolin. In particular, the present invention relates to pulverizing the kaolin twice before heat treatment or calcination.

BACKGROUND OF THE INVENTION

Kaolin is a fine usually white clay formed by the weathering of aluminous minerals (as feldspar) and mainly consists of kaolinite. Kaolinite is commonly represented by one or more of the chemical formulae $Al_4Si_4O_{10}(OH)_8$; $Al_2O_3.2SiO_2.2H_2O$; and/or $Al_2Si_2O_5(OH)_4$. Kaolin is one of the many industrial minerals mined today. Reserves are found in Georgia (USA), Egypt, Brazil, United Kingdom, Queensland (Australia), Korea, and Ukraine.

The mining of many industrial minerals in China is rapidly increasing. Kaolin is among these industrial minerals. Kaolin deposits exist in the Shanxi province of China. However, Shanxi kaolin may differ from kaolin found in other parts of the world.

Generally speaking, kaolin from different countries, and even different deposits within the same country, differs in many respects due to variations in a number of kaolinite properties. Examples of such properties include degree of crystallinity, particle size, particle shape, size and/or shape distribution.

Variations in properties lead to differences in performance of the resultant kaolin products. For example, crystallinity impacts resultant brightness, whiteness, opacity, gloss, and viscosity of the resultant products. Particle size, shape, and distribution impacts the smoothness, optical properties, and flow properties of the resultant products.

The greatest demand for kaolin based products comes from the paper industry, which uses them to coat and fill papers and boards. However, kaolin based products include paints, agricultural compositions, fiberglass products, polymer and rubber compositions, ceramic applications, catalyst supports, pharmaceuticals, cosmetics and personal care applications such as facial masks and body masks, electrical components, adhesives, filter aids, and many more. Improved processing of kaolin and improved kaolin products are likely to provide improved products that contain or employ kaolin.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Rather, the sole purpose of this summary is to present some concepts of the invention in a simplified form as a prelude to the more detailed description that is presented hereinafter.

The present invention provides processes and products that are made using Chinese kaolin, also known as Shanxi kaolin, involving pulverizing the kaolin twice before heat treatment. At least two distinct pulverization acts improves the quality of the heat treated kaolin including calcined kaolin that is produced.

One aspect of the invention relates to methods of processing Chinese kaolin involving providing Chinese kaolin having a desired particle size distribution, delaminating the Chinese kaolin, drying the delaminated Chinese kaolin, pulverizing the delaminated and dried Chinese kaolin at least two times, and heating the at least twice pulverized Chinese kaolin.

Another aspect of the invention relates to systems for automated processing of Chinese kaolin containing a pulverizer for pulverizing Chinese kaolin, a tester for testing and generating data of at least one parameter of the Chinese kaolin or at least one parameter of the pulverizer, a controller, operatively coupled to the pulverizer and the tester, for controlling operation of the pulverizer based on data received from the tester.

To the accomplishment of the foregoing and related ends, the invention comprises the features hereinafter fully described and particularly pointed out in the claims. The following description and the annexed drawings set forth in detail certain illustrative aspects and implementations of the invention. These are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

Figure 1:
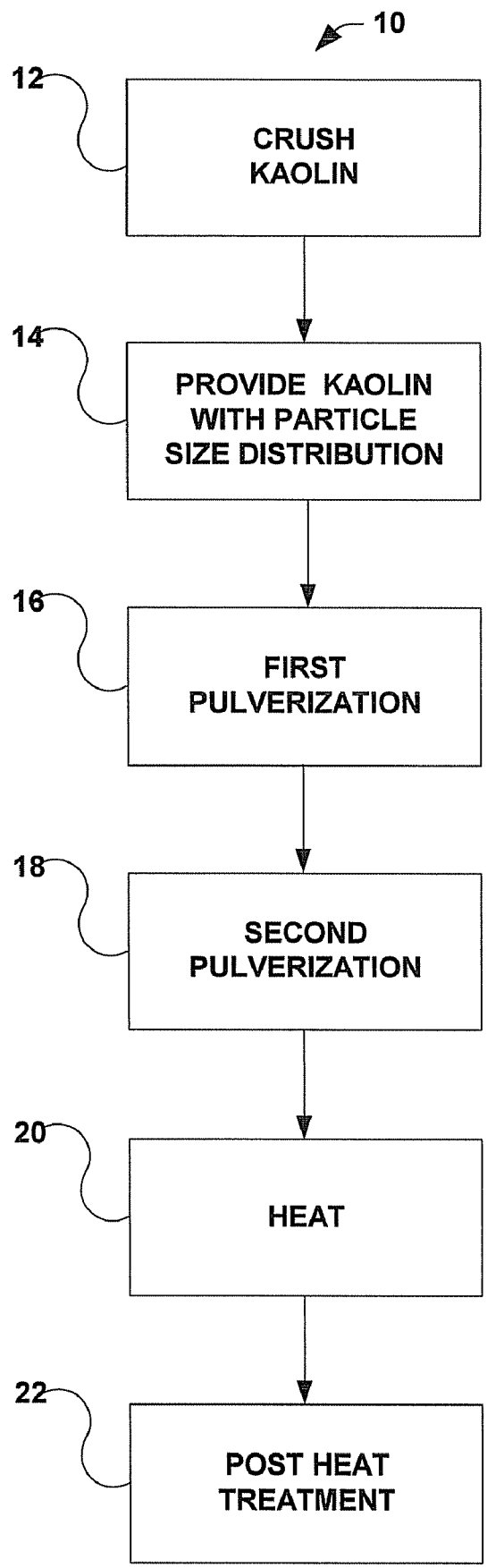
FIG. 1 is a flow diagram of one aspect of a system and method of processing Chinese kaolin in accordance with the present invention.

The kaolin processed in accordance with the present invention contains at least some Chinese Kaolin. In other words, Chinese kaolin is processed in accordance with the present invention, or a mixture of Chinese kaolin and another clay substance such as Georgian kaolin (USA) is processed in accordance with the present invention. Chinese kaolin is defined as kaolinite that is obtained from the country of China with borders defined in the year 2003. Chinese kaolin is sometimes referred to as Shanxi kaolin. It has been found that Chinese kaolin is characterized by one or more of several attributes, when compared to kaolin from Middle Georgia (USA): low titania content, low iron oxide content, a higher propensity to release alumina upon heating, high acid solubility, and high carbon content.

Chinese kaolin mined from the Earth is subjected to preliminary processing and/or beneficiation to facilitate transportation and/or storage of the raw material. While crude kaolin can be subjected to one or more of a number of preliminary processing acts, the Shanxi crude kaolin is initially crushed. Crushing reduces kaolin rock to gravel; that is, kaolin rock having diameters of less than about 10 cm in diameter. Crushers are made by the following manufacturers: Stedman, Svedala, Symons, Nordberg, Telsmith, Traylor, KVS, Allis-Chalmers, Jeffrey, Pennsylvania, American, SBM, and DFC. The particular preliminary processing employed, if any, is not critical to the present invention.

Grinding involves processing crude kaolin to achieve a desired size. Grinding may be carried out by dry milling, dry ball milling, dry grinding, and the like. Grinding aids may be added to the kaolin to facilitate grinding. When a desired powder size is achieved, subsequent delamination is employed to achieve a desired particle size.

In one embodiment, grinding is performed to provide kaolin wherein at least about 90% by weight of the kaolin has an equivalent spherical diameter of about 75 microns or less and from about 0.01% to about 90% by weight of the kaolin has an equivalent spherical diameter of about 2 microns or less. In another embodiment, grinding is performed to provide kaolin wherein at least about 90% by weight of the kaolin has an equivalent spherical diameter of about 60 microns or less and from about 0.1% to about 50% by weight of the kaolin has an equivalent spherical diameter of about 2 microns or less. In yet another embodiment, grinding is performed to provide kaolin wherein at least about 90% by weight of the kaolin has an equivalent spherical diameter of about 45 microns or less and from about 1% to about 10% by weight of the kaolin has an equivalent spherical diameter of about 2 microns or less.

There are a number of methods and devices for measuring particle sizes in this range. For the purposes of this invention particle size is determined by conventional sedimentation techniques using Micromeretics, Inc.'s SEDIGRAPH® 5100 particle size analyzer. Particles are slurried in water with a dispersant and pumped through the detector with agitation to disperse loose agglomerates.

Dry milling or grinding typically involves using energy inputs from about 5 horsepower hour per ton of dry kaolin to about 50 horsepower hour per ton of kaolin. Grinding may be carried out using apparatus such as a Raymond mill, a horizontal mill, a media mill such as a Patterson continuous ball mill in which the grinding media comprises porcelain or stainless steel balls of less than 5 inches diameter. Grinding mills are made by the following manufacturers: Raymond, Northwest, Denver, Allis-Chalmers, Marcy, Hardinge, KVS, Marion, and Traylor. Any type of dry milling that achieves the desired particle size distribution can be employed.

After the Chinese kaolin is processed so that it has a desired powder size, it is subjected to delamination. Kaolin, in most cases, contains naturally separated platy kaolin particles as well as "booklets", which comprise stacks of kaolin platelets. These stacks are concentrated in particles having a size of about 2 or more microns. Delamination of these booklets involves providing impact energy which is just sufficient to cleave apart the kaolin platelets that make up the booklets without further fracturing the kaolin platelets. In other words, delamination alters or changes kaolin having a first structure to kaolin with a second structure, different from the first structure. The resulting delaminated particles are highly crystalline. In delamination, the increase in the content of particles finer than about 2 microns particles is generally minimal.

Delamination can involve wet milling, slurry milling, wet grinding, and the like. Such delamination processes involve the use of a grinding media, and water. Kaolin is combined with the water to form slurry and transported, such as by pumping, through the delamination equipment that contain the media. Typically, the kaolin is delaminated at solids of from about 5% to about 45% by weight.

Optionally, a clay dispersant and/or fluxing agent are also added to the slurry to provide additional fluidity to facilitate processing and handling. Examples of clay dispersants include ammonia-based dispersants, phosphate-based dispersants, sulfonate dispersants, carboxylic acid dispersants, and polymeric dispersants, such as polyacrylate dispersants, as well as other organic dispersants employed in kaolin pigment processing. The amount of dispersant used in the slurry is typically from about 0.01% to about 1% based on the weight of kaolin.

The grinding media is a relatively dense, hard particulate material which does not substantially discolor the clay, or charge or leave objectionable residues in the ground clay. For example, the density of the grinding media is at least about 1.5. Examples of grinding media include glass beads, alumina, zirconia, small ceramic balls or beads, coarse sand, plastic cylinders, stainless steel beads, beads or pellets of nylon, styrene-divinyl benzene copolymer, polyethylene or other hard plastic, and the like.

The volume of beads to clay in the slurry is sufficient to effect delamination. In one embodiment, the slurry of at least water, kaolin, and grinding media contains from about 10% to about 70% by volume of grinding media. In another embodiment, the slurry contains from about 25% to about 50% by volume of grinding media.

An exemplary suitable vessel used for delamination contains vertical baffles. Such a vessel can be equipped with an agitation system containing multiple agitator elements attached to a vertical shaft. The number and spacing of the agitators varies, but is selected for the specific process conditions in order to impart the necessary combined shear and percussive and frictional energy input necessary to overcome the Van der Waals forces holding individual platelets in a stacked array or booklet. Energy input required for delamination varies due to differences between specific kaolin crudes, process conditions, and equipment; typically, requiring 5 to 75 horsepower hour per ton of kaolin charged to the delaminators.

The resultant slurry of delaminated kaolin contains more fine particles of kaolin. In one embodiment, the resultant slurry of delaminated kaolin contains at least about 60% by weight of kaolin having an equivalent spherical diameter of about 2 microns or less. In another embodiment, the resultant slurry of delaminated kaolin contains at least about 80% by weight of kaolin having an equivalent spherical diameter of about 2 microns or less. In yet another embodiment, the resultant slurry of delaminated kaolin contains at least about 90% by weight of kaolin having an equivalent spherical diameter of about 2 microns or less. In still yet another embodiment, the resultant slurry of delaminated kaolin contains at least about 94% by weight of kaolin having an equivalent spherical diameter of about 2 microns or less.

Screening can be employed to remove the milling media, and optionally, can be employed to remove particles larger than 40 microns. Filtration can also be employed to effectively remove water prior to spray drying. The kaolin is optionally washed during this stage. Optionally, fractionation can be employed to separate the coarse particles. In this connection, a certrifuge may be used to perform the water separation.

After delamination, water is removed from the delaminated kaolin to dry the kaolin. The kaolin is dried by any suitable technique. Examples of drying kaolin include spray drying, flash drying, rotary drying, or other conglomeration techniques. These drying techniques are known in the clay industry.

Drying the kaolin is performed to reduce the moisture level of the kaolin, in part, to facilitate subsequent heat treatments. In one embodiment, after drying, the kaolin has a moisture level of less than about 5% by weight. In another embodiment, the kaolin has a moisture level of less than about 1.5% by weight. In yet another embodiment, the kaolin has a moisture level of less than about 1% by weight. In still yet another embodiment, the kaolin has a moisture level of less than about 0.5% by weight.

Prior to heat treatment, such as calcinations, and generally after the crude kaolin has a desired equivalent spherical diameter, the kaolin is pulverized in at least two separate acts (twice pulverized). One pulverization treatment, or a pulverization treatment for longer than usual time is not sufficient. At least two distinct pulverization treatments are performed on the kaolin ready for heat treatment. In one embodiment, the kaolin is pulverized in at least three separate acts (thrice pulverized). In another embodiment, the kaolin is pulverized in at least five separate acts (four times pulverized). In yet another embodiment, the kaolin is pulverized in at least seven separate acts (five times pulverized). In still yet another embodiment, the kaolin is pulverized in at least nine separate acts (seven times pulverized).

The first pulverization is believed to break up any agglomerates that may be present. Such agglomerates may form during drying, changing the particle size achieved by delamination. Chinese kaolin has a relatively high amount of carbon therein. Although not wishing to be bound by any theory, it is believed that the second pulverization act serves to expose carbon from within the kaolin so that it may be consumed during subsequent heating. The at least two pulverization acts therefore serves to provide one or more of a certain particle size, a certain shape for the kaolin particles, kaolin particles where carbon therein is exposed, and kaolin that undergoes desirable thermal structuring under application of heat.

The two or more pulverization acts provides kaolin wherein at least about 80% by weight has an average particle diameter of about 2 microns or less. In another embodiment, the two or more pulverization acts provides kaolin wherein at least about 90% by weight has an average particle diameter of about 2 microns or less. In yet another embodiment, the two or more pulverization acts provides kaolin wherein at least about 93% by weight has an average particle diameter of about 2 microns or less. In still yet another embodiment, the two or more pulverization acts provides kaolin wherein at least about 95% by weight has an average particle diameter of about 2 microns or less. Moreover, the two or more pulverization acts provides kaolin wherein at least about 60% by weight has an average particle diameter of about 1 micron or less. In another embodiment, the two or more pulverization acts provides kaolin wherein at least about 70% by weight has an average particle diameter of about 1 micron or less. In yet another embodiment, the two or more pulverization acts provides kaolin wherein at least about 80% by weight has an average particle diameter of about 1 micron or less.

The two or more pulverization acts provides kaolin with a reduced bulk density. In one embodiment, the bulk density of the at least twice pulverized kaolin is at least about 25% less than the bulk density prior to the two or more pulverization acts. In another embodiment, the bulk density of the at least twice pulverized kaolin is at least about 40% less than the bulk density prior to the two or more pulverization acts. In yet another embodiment, the bulk density of the at least twice pulverized kaolin is at least about 50% less than the bulk density prior to the two or more pulverization acts.

General types of pulverizers that can be employed for pulverizing include Bowl, Hammer, Ball & Race type, IMP, Double Cone, Screen Type Roller Mill, and Roller Mill. Pulverizing can be carried out in a high energy impact mill, such as a Hurricane® mill; a Bauer hammer mill available from C.E. Bauer Co. of Chicago, III; a Mikro Mill available from Pulverization Machinery Company; a Mikro Sampimill available from Hosokawa Micron Powder Systems; or a Mikro-Pulverizer hammer mill also available from Hosokawa Micron Powder Systems. Other pulverizers are made by the following manufacturers: Alpine, Williams, Raymond, Bradley, Riley, and B & W.

After pulverization, optionally additional milling and classifying is effected by passing the twice pulverized kaolin through an air classifying mill which contains an impact rotor for attriting the twice pulverized kaolin and an integral vane rotor classifier for classifying the attrited material and recycling particles that exceed a desired size, which may vary depending upon the application of the resultant kaolin product produced in accordance with the present invention. For example, twice pulverized kaolin particles that are larger than about 40 microns may be removed from the kaolin being processed. The impact rotor can be provided with bars at which the twice pulverized kaolin is impacted. Oversized twice pulverized kaolin rejects from the air classifier mill may be separated in a cyclone separator, and returned to the air classifier mill for further milling or subjected to additional grinding and/or pulverizing.

An exemplary air classifying mill is the Mikro ACM pulverizer. In this mill, the twice pulverized kaolin is advanced by a screw conveyer and first impacts at the pins of the pin rotor. Particles are entrained by an air stream which enters below the pin rotor and are carried up between the inner wall and the shroud ring with baffles which decrease air swirl. Particles are then deflected inward by an air dispersing ring to a vane rotor classifier. The rotor is separately driven through a speed control which may be adjusted independently of the pin rotor speed. Acceptable particles pass upward through the exhaust and to a collector. Oversize particles are carried downward by the internal circulating air stream and are returned to the pin rotor for a further reduction. Other Classifiers are made by the following manufacturers: Alpine, Alfa Laval/Sharples, Wemco, Krebs, EIMCO, Dorr-Oliver, Denver, and Pan-O-Matic.

After the kaolin is pulverized at least twice, it is subjected to heat treatment. When kaolin is heated, it undergoes a series of characteristic changes, detectable by various methods including differential thermal analysis (DTA). Heat treatment may be employed to form one or more of metakaolin, partially calcined kaolin, and calcined kaolin, depending on the temperatrure/duration of the heat treatment. Heat treatment is performed under one of an inert atmosphere, an oxidizing atmosphere, and a reducing atmosphere.

For example, after heating from about 450 to about 650° C. for a sufficient period of time, kaolin undergoes a strongly endothermic dehydration reaction resulting in the starting of conversion to material known as metakaolin. The metakaolin state is conveniently ascertained by acid solubility testing because the alumina in the clay is virtually completely soluble in strong mineral acid.

Calcining destroys the crystallinity of hydrous kaolin and renders the kaolin substantially amorphous. Calcination occurs after heating at temperatures in the range from about 700 to about 1200° C. for a sufficient period of time. Commercial vertical and horizontal rotary calciners can be used to produce metakaolin, partially calcined kaolin, and/or calcined kaolin. Operation is controlled to avoid calcining at sufficiently high temperatures to form unwanted mullite ($3Al_2O_3 \cdot SiO_2$).

In one embodiment, the at least twice pulverized kaolin is heated to a temperature from about 450 to about 1200° C. for a time from about 1 minute to about 10 hours. In another embodiment, the at least twice pulverized kaolin is heated to a temperature from about 500 to about 1100° C. for a time from about 10 minutes to about 5 hours. In a specific embodiment, the at least twice pulverized kaolin is heated to a temperature from about 475 to about 700° C. for a time from about 5 minutes to about 6 hours. In another specific embodiment, the at least twice pulverized kaolin is heated to a temperature from about 750 to about 1050° C. for a time from about 15 minutes to about 4 hours.

After heat treatment, again optionally additional milling and classifying is effected by passing the heat treated kaolin through an air classifying mill which contains an impact rotor for attriting the heat treated kaolin and an integral vane rotor classifier for classifying the attrited material and recycling particles that exceed a desired size, which may vary depending upon the application of the resultant kaolin product produced in accordance with the present invention. For example, heat treated kaolin particles that are larger than about 20 microns may be removed from the kaolin being processed. The impact rotor can be provided with bars at which the heat treated kaolin is impacted. Oversized heat treated kaolin rejects from the air classifier mill may be separated in a cyclone separator, and returned to the air classifier mill for further milling or subjected to additional grinding and/or pulverizing.

For example, after heat treatment, another pulverization/classification act may be performed to remove particles that have a size greater than about 45 microns. In another embodiment, the additional pulverization/classification act may be performed to remove particles that have a size greater than about 30 microns. In yet another embodiment, the additional pulverization/classification act may be performed to remove particles that have a size greater than about 20 microns.

Generally speaking, one or more conventional clay processing steps such as selective flocculation, flocc/filtration, and the like, may be employed before or after the multiple pulverizations and heat treatment.

The Chinese kaolin processed in accordance with the present invention may have a higher opacity than conventionally processed Chinese kaolin (not pulverized prior to heat treatment, or only one pulverization prior to heating). Also, the Chinese kaolin processed in accordance with the present invention may have a higher brightness at any given calcination/heating temperature than conventionally processed Chinese kaolin at comparable calcinations temperatures. In one embodiment, the Chinese kaolin processed in accordance with the present invention and calcined produces material that has a brightness of at least about 86. In another embodiment, the Chinese kaolin processed in accordance with the present invention and calcined produces material that has a brightness of at least about 90. In yet embodiment, the Chinese kaolin processed in accordance with the present invention and calcined produces material that has a brightness of at least about 95. In still yet embodiment, the Chinese kaolin processed in accordance with the present invention and calcined produces material that has a brightness of at least about 96. In another embodiment, the Chinese kaolin processed in accordance with the present invention and calcined produces material that has a brightness of at least about 82.

The Chinese kaolin processed in accordance with the present invention may have a relatively high surface area compared to conventionally processed Chinese kaolin. The relatively high surface area contributes to the high opacity of the resultant Chinese kaolin by increasing the light scattering effects thereof. In one embodiment, the Chinese kaolin processed in accordance with the present invention has an oil absorption of about 60 or more. In another embodiment, the Chinese kaolin processed in accordance with the present invention has an oil absorption of about 80 or more. In yet another embodiment, the Chinese kaolin processed in accordance with the present invention has an oil absorption of about 85 or more. In still yet another embodiment, the Chinese kaolin processed in accordance with the present invention has an oil absorption of about 90 or more. Surface area is determined using Gardner Coleman Oil Absorption Test is based on ASTM D-1483-84 which measures grams of oil absorbed per 100 grams of kaolin.

Referring to FIG. 1, a high level diagram of various aspects of a Chinese kaolin processing methodology 10 is shown. In act 12, crude Chinese kaolin is crushed, thereby facilitating transportation and storage from the mining site. In act 14, the kaolin is processed to achieve a desired particle size. Such processing may include one or more of grinding, crushing, delaminating, drying, standard clay beneficiation acts, and the like. Achieving the desired particle size facilitates subsequent processing.

After a certain desired particle size of kaolin is obtained, act 16 involves the first of at least two pulverization acts. Act 18 is the second of at least two pulverization acts. Optionally, additional pulverization acts may be performed before the Chinese kaolin is heated. The multiple pulverization acts not only to provide Chinese kaolin having desired properties, but it also exposes carbon on the surface of the carbon rich Chinese kaolin particles.

Act 20 involves heating the at least twice pulverized kaolin to convert the kaolin to one or more of metakaolin, partially calcined kaolin, and calcined kaolin. Act 22 contemplates one or more procedures includes pulverization, grinding, screening, packaging, and the like.

Figure 2:
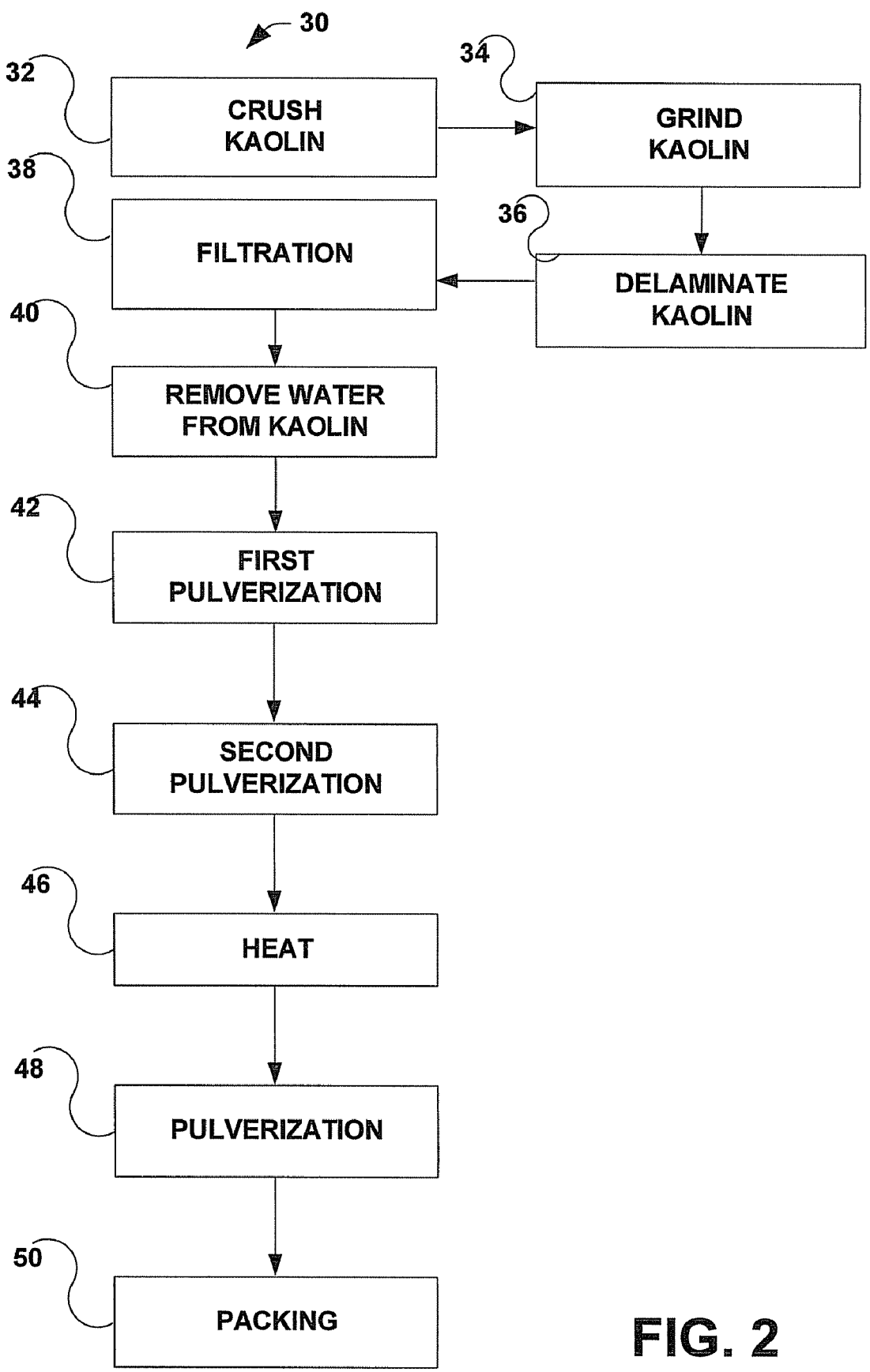
FIG. 2 is a flow diagram of another aspect of a system and method of processing Chinese kaolin in accordance with the present invention.

Referring to FIG. 2, a more detailed diagram of various aspects of a Chinese kaolin processing methodology 30 is shown. In act 32, crude Chinese kaolin is crushed, thereby facilitating transportation and storage from the mining site. In act 34, grinding, such as dry milling, is performed so that the kaolin has a desired size or particles exceeding a certain size are removed. Act 36 involves delaminating the kaolin by, for example, slurry milling, to disassemble the "booklets" into "pages". Act 38 involves screening to at least one of remove wet milling media and remove particles that exceed a certain size. In act 40, water is removed from the kaolin, for example, by spray or rotary drying.

After drying kaolin, act 42 involves the first of at least two pulverization acts. If in act 40 water is removed from the kaolin by spray drying, agglomerates may form. Act 42 serves to break up these agglomerates. Act 44 is the second of at least two pulverization acts. Optionally, additional pulverization acts may be performed before the Chinese kaolin is heated. The multiple pulverization acts not only provide Chinese kaolin having desired properties, but it also exposes carbon on the surface of the carbon rich Chinese kaolin particles.

Act 46 involves heating the at least twice pulverized kaolin to convert the kaolin to one or more of metakaolin, partially calcined kaolin, and calcined kaolin. Act 48 involves pulverizing the one or more of metakaolin, partially calcined kaolin, and calcined kaolin to achieve a desired particle size distribution. Act 50 involves packaging the one or more of metakaolin, partially calcined kaolin, and calcined kaolin having the desired properties.

Figure 3:
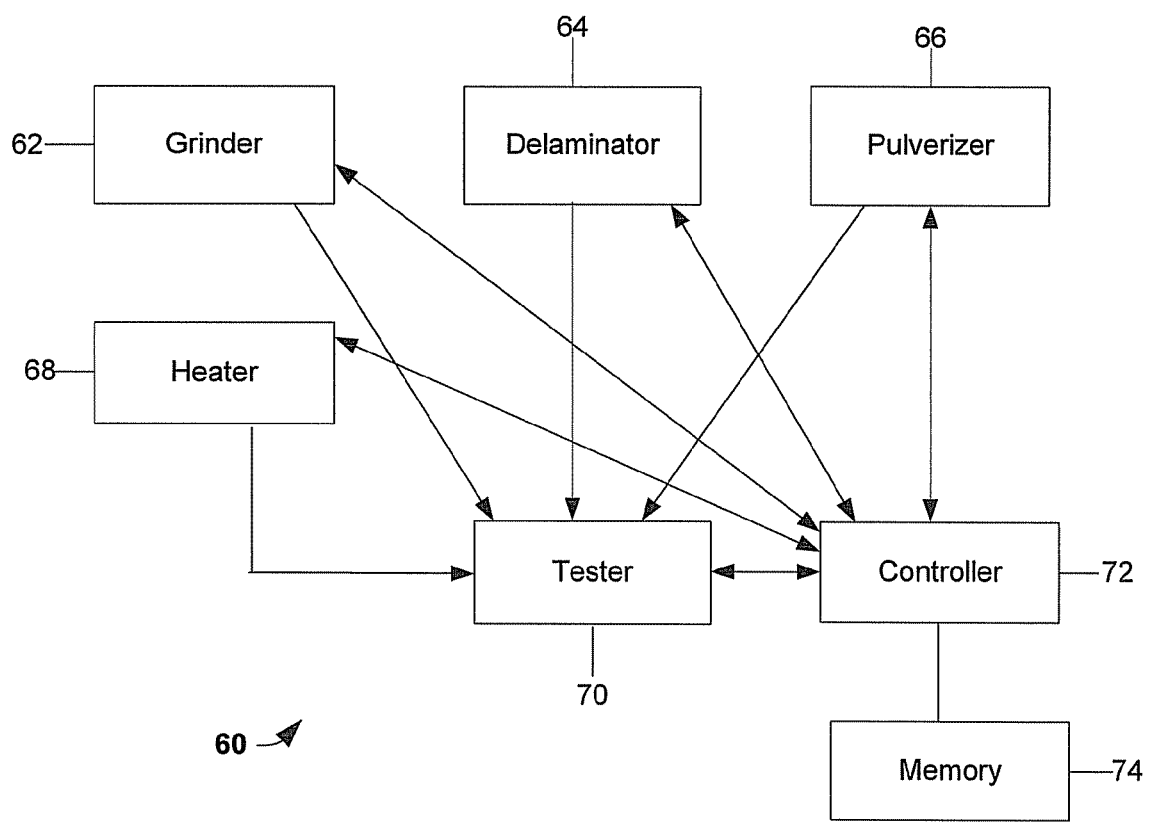
FIG. 3 is a schematic diagram of another aspect of a system for automated processing of Chinese kaolin in accordance with the present invention.

Referring to FIG. 3, a system 60 to process Chinese kaolin is shown. The system includes one or more of a grinder 62, delaminator 64, pulverizer 66, and heater 68 coupled to a tester 70 and a controller 72. The grinder 62 processes kaolin by providing kaolin with desired size, the delaminator 64 breaks apart the "booklet structure" of hydrous kaolin, the pulverizer 66 also provides kaolin with desired properties and/or gets carbon with the kaolin to the surface of the kaolin particles, and the heater 68 heats the kaolin to provide one or more of metakaolin, partially calcined kaolin, and calcined kaolin. The tester 70 can be any device that measures at least one parameter associated with the kaolin (such as particle size distribution, brightness, whiteness, roughness, % moisture content, % content of particular chemical, and the like) or any parameter associated with any one of the grinder 62, delaminator 64, pulverizer 66, and heater 68 (such as the temperature with the heater 68 or the work imposed in the grinder 62).

While any one of the grinder 62, delaminator 64, pulverizer 66, and heater 68 are operating, the tester 70 tests the kaolin being processed. For example, while the grinder 62, delaminator 64, or pulverizer 66 is operating, a sample of kaolin may be withdrawn and tested to determine a parameter, such as particle size distribution. The tester 70 sends the data generated by the testing to the controller 72, which is adapted to receive such kaolin parameter data from the tester 70. Alternatively, the tester 70 may measure a parameter of the grinder 62, delaminator 64, pulverizer 66, and heater 68, and send data associated with the parameter to the controller.

The controller 72 analyzes such data, and based on the analysis, sends a signal to any of the grinder 62, delaminator 64, pulverizer 66, and heater 68 to either continue the process, modify the process, or terminate the process. To facilitate such analysis, a data store or memory 74 may be coupled to the controller 72 so that the controller 72 can compare data sent by the tester 70 to stored data. The controller 72 may send a signal to the tester 70 to perform a test. Examples of ways in which the controller 72 can modify a process include increasing or decreasing the temperature in the heater 68; increasing or decreasing the work/energy required by any of the grinder 62, delaminator 64, or pulverizer 66; continue operating any of the grinder 62, delaminator 64, or pulverizer 66 to achieve a certain desired particle size distribution; directing a repeat of an act such as requiring a third pulverization act; and the like.

The following examples illustrate the present invention. Unless otherwise indicated in the following examples and elsewhere in the specification and claims, all parts and percentages are by weight, all temperatures are in degrees Centigrade, and pressure is at or near atmospheric pressure.

COMPARATIVE EXAMPLE 1

Chinese kaolin is crushed to 2-3 cm diameter rocks, dry milled to reduce kaolin to −325 mesh or 44 microns powder. The powder is then delaminated, using ceramic beads, in water with the help of a phosphate dispersant to produce particles with 94% by weight less than 2 microns. After screening, the kaolin slurry is spray dried to reduce moisture to less than 1% by weight. The spray-dried kaolin is then pulverized product is then calcined to temperatures that may reach 1100° C. The calcined product is finally pulverized to grind oversize aggregates formed during calcination. Approximate particle size of the intermediates and final products are shown below in Table 1, as well as typical physical properties in Table 2:

TABLE 1

| Micron, less than | dry-milled product % | calcination feed % | final products % |
|---|---|---|---|
| 50 | 99.5 | 98.7 | 101.6 |
| 10 | 52.5 | 99.9 | 99.4 |
| 5 | 39 | 98.7 | 97.4 |
| 2 | 26.3 | 93.3 | 87.6 |
| 1 | 20.4 | 78.8 | 69.1 |
| 0.5 | 14.8 | 55.6 | 34.2 |
| 0.3 | 10 | 37.8 | 12.9 |
| 0.2 | 7.4 | 27.1 | 7.1 |

TABLE 2

| Sample | % carbon (avg. of 2) | total acid solubility (TAS) | Brightness | surface area $g/m^2$ |
|---|---|---|---|---|
| Calcination Feed | 2.16 | NA | NA | NA |
| Calcination Product | 0.014 | 12.26 | 95.5 | 14.86 |

EXAMPLE 1

Chinese kaolin is crushed to 2-3 cm diameter rocks, dry milled to reduce kaolin to −325 mesh or 44 microns powder. The powder is then delaminated, using ceramic beads, in water with the help of a phosphate dispersant to produce particles with 94% by weight less than 2 microns. After screening, the kaolin slurry is spray dried to reduce moisture to less than 1% by weight. The spray-dried kaolin is then pulverized twice (passed through two pulverizers). The twice-pulverized product is then calcined to temperatures that may reach 975° C. The calcined product is pulverized again to grind oversize aggregates formed during calcination. Selected physical properties of the product are shown in Table 3 (such as particle size distribution average, brightness, and the oil absorption values):

TABLE 3

| size | Example 1 |
|---|---|
| <2 microns | 85% by wt. |
| <1 micron | 69% by wt. |
| <0.5 microns | 43% by wt. |
| Brightness | 95 |
| PSD ave. | 0.58 microns |
| oil absorption | 95.5 |

EXAMPLE 2

Chinese kaolin is crushed to 2-3 cm diameter rocks, dry milled to reduce kaolin to −325 mesh or 44 microns powder. The powder is then delaminated, using ceramic beads, in water with the help of a phosphate dispersant to produce particles with 94% by weight less than 2 microns. After screening, the kaolin slurry is spray dried to reduce moisture to less than 1% by weight. The spray-dried kaolin is then pulverized twice (either passed through two pulverizers or passed twice through one pulverizer). The twice-pulverized product is then calcined to temperatures that may reach 920 to 975° C. The product has a brightness of about 96. The calcined product is pulverized again to grind oversize aggregates formed during calcination. Selected physical properties of the product are shown in Table 4 (such as particle size distribution average, brightness, and the oil absorption values):

TABLE 4

| size | Example 2 |
|---|---|
| <2 microns | 85% by wt. |
| <1 micron | 66% by wt. |
| <0.5 microns | 32% by wt. |
| Brightness | 96 |
| PSD ave. | 0.68 microns |
| oil absorption | 96.2 |

EXAMPLE 3

Products of Comparative Example 1 and Examples 1 and 2 are evaluated in a PVC 55 (Pigment Volume Concentration, 55% by weight pigment in paint) paint evaluation. Paint testing is commonly used to compare the hiding power (opacity) and other important properties such as whiteness, yellowness, and gloss. The properties of each paint Chinese kaolin mixture are reported in Table 5.

TABLE 5

| Paint Property | Com. Ex. 1 | Example 1 | Example 2 |
|---|---|---|---|
| Viscosity KU @ 77° F.: | 104 | 104 | 104 |
| pH: | 8.7 | 8.3 | 8.3 |
| C. Ratio 1.5 mills: | 91.7 | 93.4 | 93.4 |
| C. Ratio 3 mils: | 96.9 | 97.9 | 98.1 |
| Reflectance: | 91.6 | 92.2 | 92.1 |
| Whiteness: | 87.3 | 87.7 | 87.7 |
| Yellowness: | 1.7 | 1.9 | 1.8 |
| Hunter L: | 97.1 | 97.4 | 97.3 |
| Hunter a: | −0.8 | −0.6 | −0.6 |
| Hunter b: | 1.2 | 1.3 | 1.2 |
| Gloss @ 60 deg: | 2.3 | 2.2 | 2.2 |
| Sheen @ 85 deg: | 5.9 | 5.9 | 5.2 |
| Tint Strength: | 51.2 | 53.9 | 53.9 |

EXAMPLE 4

Chinese kaolin is crushed to 2-3 cm diameter rocks, dry milled to reduce kaolin to −325 mesh or 44 microns powder. The powder is then delaminated, using ceramic beads, in water with the help of a phosphate dispersant to produce particles with 94% by weight less than 2 microns. After screening, the kaolin slurry is spray dried to reduce moisture to less than 1% by weight. The spray-dried kaolin is then pulverized twice (either passed through two pulverizers or one pulverizer twice). The twice-pulverized product is then calcined to temperatures that may reach 815 to 900° F. The products have a brightness of about 92. The calcined product is pulverized again to grind oversize aggregates formed during calcination. Selected physical properties of the product are shown in Table 6 (such as particle size distribution average, brightness, and the oil absorption values):

TABLE 6

| size | Example 4 |
|---|---|
| <2 microns | 86% by wt. |
| pH | 5.9 |
| Brightness | 92 |

TABLE 6-continued

| size | Example 4 |
|---|---|
| PSD ave. | 0.68 microns |
| oil absorption | 74 |

EXAMPLE 5

Product of Example 4 is evaluated in a PVC 66 (Pigment Volume Concentration, 66% by weight pigment in paint) paint evaluation. Paint testing is commonly used to compare the hiding power (opacity) and other important properties such as whiteness, yellowness, and gloss. In this testing, the Chinese kaolin is evaluated against Georgia (USA) kaolin, Satintone® 5 HB available from Engelhard Corporation. Conventional wisdom dictates that USA kaolin is superior in coating performance to kaolin from anywhere else in the world. The properties of each paint kaolin mixture are reported in Table 7.

TABLE 7

| PVC66 Property | Example 4 | Satintone ® 5 HB USA Kaolin |
|---|---|---|
| Viscosity KU @ 77° F.: | 100 | 91 |
| pH: | 8.8 | 9.0 |
| C. Ratio 1.5 mills: | 93.9 | 94.3 |
| C. Ratio 3 mils: | 98.5 | 98.4 |
| Reflectance: | 92.0 | 92.0 |
| Whiteness: | 87.6 | 86.2 |
| Yellowness: | 1.9 | 2.6 |
| Hunter L: | 97.3 | 97.5 |
| Hunter a: | −0.5 | −0.8 |
| Hunter b: | 1.2 | 1.7 |
| Gloss @ 60 deg: | 2.3 | 2.5 |
| Sheen @ 85 deg: | 6.5 | 13.0 |
| Tint Strength: | 53.4 | 53.6 |

EXAMPLE 6

Chinese kaolin is crushed to 2-3 cm diameter rocks, dry milled to reduce kaolin to −325 mesh or 44 microns powder. The powder is then delaminated, using ceramic beads, in water with the help of a phosphate dispersant to produce particles with 94% by weight less than 2 microns. After screening, the Chinese kaolin is fractionated to provide kaolin where 90% by weight has an average particle size diameter of 1 micron or less. After fractionation, the sample is spray dried and pulverized either 3, 5, or 7 times. The pulverized samples are calcined at 1982° C. for one hour and pulverized twice again to provide the final products.

Figure 4:
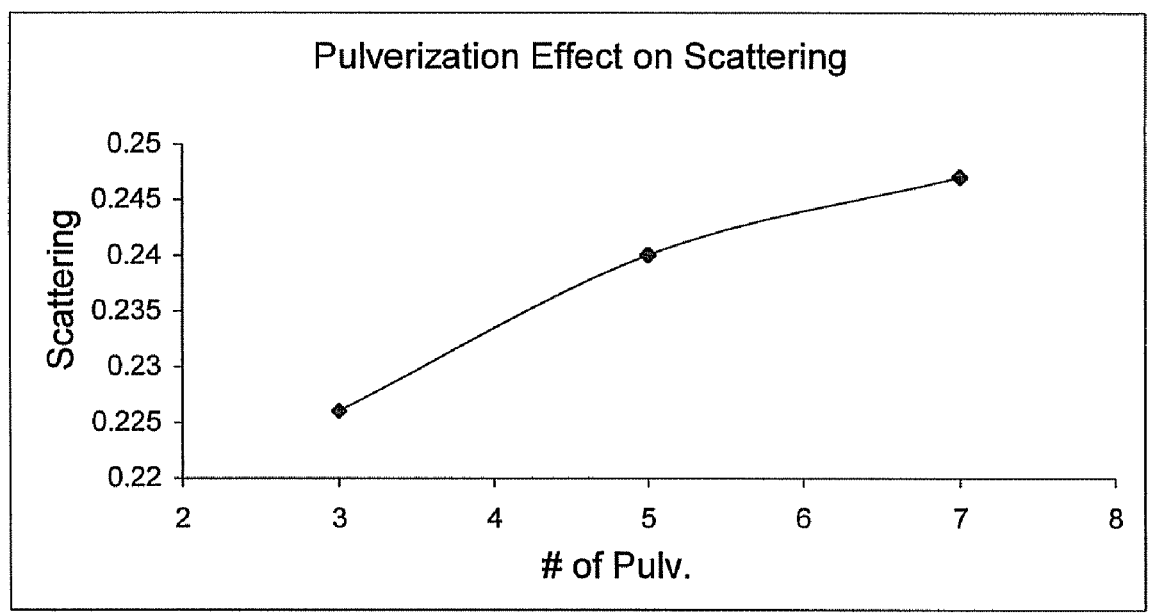
FIG. 4 is a graphical illustration plotting the number of pre-heating pulverization acts versus black glass scattering.

Referring to FIG. 4, a graphical illustration of the beneficial effect that multiple pre-heating pulverization acts have on scattering (black glass scattering) is shown. The graph indicates that improved and higher scattering is achieved by increasing the number of pre-heating pulverization acts. Higher scattering corresponds to higher opacity.

Black glass scattering is described in Kaliski, A., TAPPI, Vol. 53, No. 11, November 1970, pages 2077-2084 titled "Performance of Some Clays in Starch Containing Paper-Coating Films; Part I. Black Glass Plates as Model Substrates". Generally speaking, black glass scattering is conducted by coating a kaolin slurry containing 30% solids, by weight onto a black glass plate at a coat weight of 2-6 g/m² (expressed as dry pigment). The reflectance values of the coatings after air drying is measured at a wavelength of 457 nm by means of an Elrepho reflectometer. The reflectance values are converted by the use of Kubelka-Munk equations to light scattering coefficients ($m^2/g$). The light scattering coefficients give an indication of the opacifying potential of the kaolin. The higher the values of light scattering coefficients, the rarer is the light passing through the kaolin coating or the larger is the reflected and back scattered light. Apparently, the wavelength of 457 nm corresponds to the wavelength used in the TAPPI brightness and opacity test method.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A system for automated processing of Chinese kaolin, comprising
    a pulverizer for pulverizing Chinese kaolin;
    a tester for testing and generating data of at least one parameter of the Chinese kaolin or at least one parameter of the pulverizer, the tester coupled to the pulverizer;
    a controller, operatively coupled to the pulverizer and the tester, for controlling operation of the pulverizer based on data received from the tester, the controller further coupled to a memory; and
    a delaminator operatively coupled to the tester and the controller.

2. The system of claim 1, wherein the tester comprises a device that measures particle size distribution.

3. The system of claim 1, wherein the parameter of the Chinese kaolin comprises at least one of particle size distribution, brightness, whiteness, roughness, percent moisture content, or percent content of a particular chemical.

4. The system of claim 1, wherein the parameter of the Chinese kaolin comprises particle size distribution.

5. The system of claim 1, wherein the parameter of the pulverizer comprises at least one of energy input and number of pulverization acts.

6. The system of claim 1,further comprising a grinder operatively coupled to the tester and the controller.

7. The system of claim 1, further comprising a heater operatively coupled to the tester and the controller.

8. The system of claim 1, wherein the controller is operative to send a signal to the tester to perform a test.

9. The system of claim 1, wherein the controller is operative to send a signal to the pulverizer to perform an additional pulverization act.

10. The system of claim 1, wherein the memory comprises stored data that can be compared to data generated by the tester.

11. A system for automated processing of Chinese kaolin, comprising
    a pulverizer for pulverizing Chinese kaolin, the Chinese kaolin having a higher carbon content, a lower iron oxide content, and a higher propensity to release alumina upon heating compared to Middle Georgia (U.S.A.) kaolin;
    a tester for testing and generating data of at least one parameter of the Chinese kaolin or at least one parameter of the pulverizer, the tester coupled to the pulverizer;
    a controller, operatively coupled to the pulverizer and the tester, for controlling operation of the pulverizer based on data received from the tester, the controller further coupled to a memory; and
    a delaminator operatively coupled to the tester and the controller.

12. The system of claim 11, wherein the tester comprises a device that measures particle size distribution.

13. The system of claim 11, wherein the parameter of the Chinese kaolin comprises at least one of particle size distribution, brightness, whiteness, roughness, percent moisture content, or percent content of a particular chemical.

14. The system of claim 11, wherein the tester tests and generates data for the at least one parameter of the Chinese kaolin comprising particle size distribution.

15. The system of claim 11, wherein the parameter of the pulverizer comprises at least one of energy input and number of pulverization acts.

16. The system of claim 11, further comprising a grinder operatively coupled to the tester and the controller.

17. The system of claim 11, wherein the tester tests and generates data for the at least one parameter of the Chinese kaolin comprising carbon content.

18. The system of claim 11, wherein the controller is operative to send a signal to the pulverizer to perform an additional pulverization act.

19. The system of claim 11, wherein the memory comprises stored data that can be compared to data generated by the tester.

20. The system of claim 11, further comprising a heater operatively coupled to the tester and the controller.

* * * * *